United States Patent [19]

Longsworth

[11] 4,283,948

[45] Aug. 18, 1981

[54] CRYOGENIC AIR SAMPLER

[75] Inventor: Ralph C. Longsworth, Allentown, Pa.

[73] Assignee: Air Products and Chemicals, Inc., Allentown, Pa.

[21] Appl. No.: 106,218

[22] Filed: Dec. 21, 1979

[51] Int. Cl.$^3$ .............................................. G01N 1/24
[52] U.S. Cl. .................................. 73/863.11; 62/55.5; 73/864.51
[58] Field of Search ................ 73/421.5 R; 62/55, 45, 62/55.5

[56] References Cited

U.S. PATENT DOCUMENTS

| | | | |
|---|---|---|---|
| 3,472,038 | 10/1969 | Staas | 62/45 |
| 3,938,391 | 2/1976 | Winkler | 73/421.5 |
| 4,195,524 | 4/1980 | Hansen | 73/421.5 |

Primary Examiner—S. Clement Swisher
Attorney, Agent, or Firm—James C. Simmons; E. Eugene Innis

[57] ABSTRACT

Environmental gases, e.g. air are collected in an apparatus wherein a sample bottle containing a metering orifice for admitting the gas is contained within and cooled by a bath of liquid cryogen thus creating a partial vacuum inside the bottle to draw gas into the bottle where it is condensed and stored. The apparatus includes a source of cryogenic refrigeration disposed in an evacuated space above the liquid cryogen to condense liquid cryogen boil-off. By combining evacuation and cryogenic refrigeration the sample bottle holder can be rapidly cooled to operating temperature.

5 Claims, 3 Drawing Figures

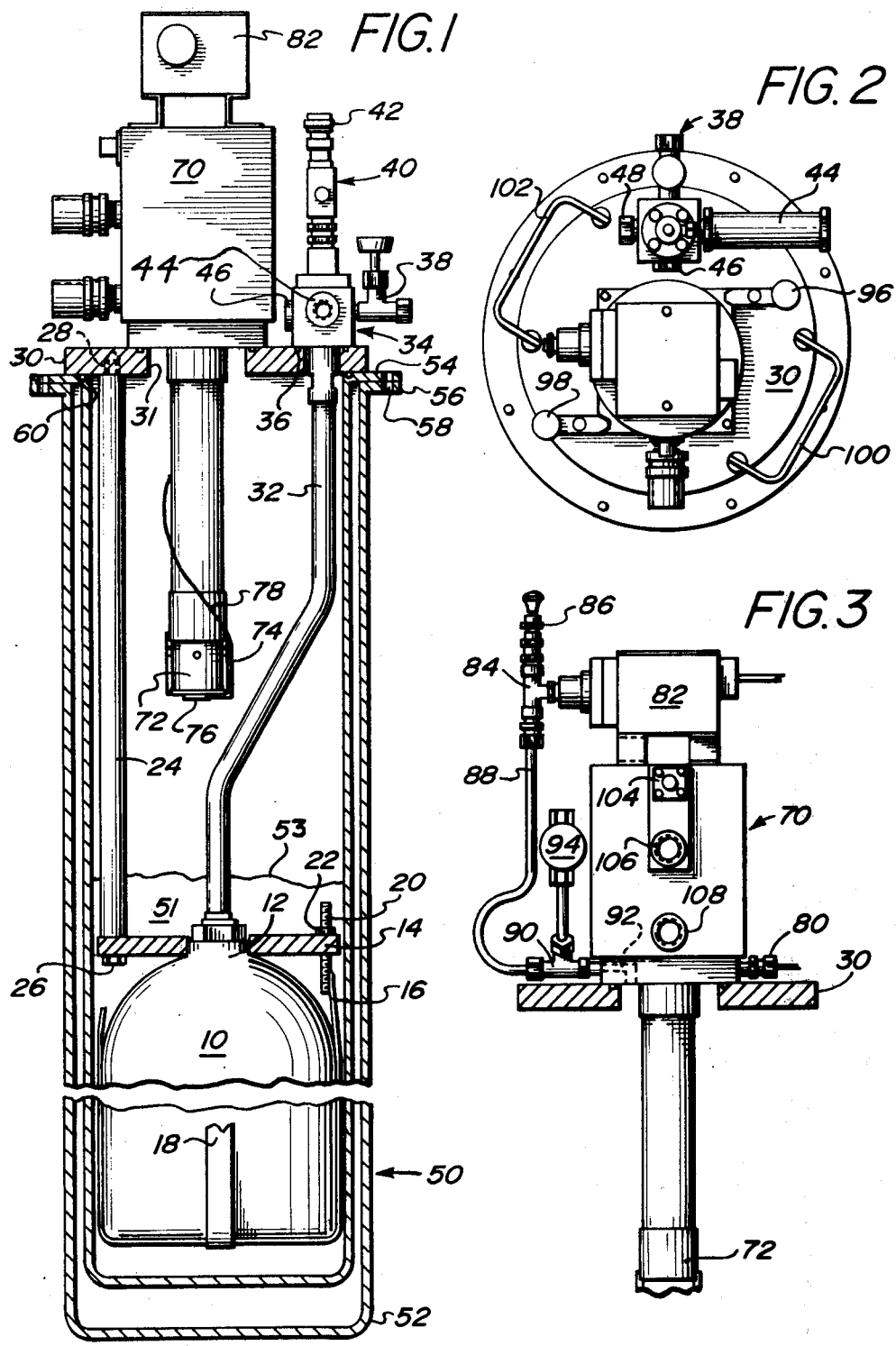

CRYOGENIC AIR SAMPLER

BACKGROUND OF THE INVENTION

1. Field of the Invention

This invention pertains to an apparatus for collecting and storing a sample of an environmental gas such as air. Each day man is becoming more and more concerned with his environment and particularly the air he breathes. In order to monitor the quality of the air, air sampling devices are utilized to draw in a quantity of the air which is confined to a storage receptacle and subsequently withdrawn form the storage receptacle in the laboratory where it can be checked for noxious and toxic elements by means of a gas analyzer.

2. Description of the Prior Art

The present invention is an improvement of the device disclosed in U.S. Patent Application Ser. No. 956,312, filed Oct. 31, 1978, now U.S. Pat. No. 4,195,524 drawn to a "Method and Apparatus for Collecting and Storing Environmental Gases". In the device of the application a sample bottle is cooled by means of a cryogenic refrigerator to create a partial vacuum within the sample bottle so that an air sample can be drawn through a metering orifice (valve) into the sample bottle where it is condensed and refrigerated until the bottle is full. After the bottle is full the entire apparatus is taken to the laboratory where the sample bottle can be warmed and the sample withdrawn for analysis. The cryogenic refrigerator being fixed to the bottle necessitates the entire apparatus being taken to the laboratory.

The device of the patent application was an improvement over the most common method of sampling environmental gases which consists of utilizing a conventional compressor to force the environmental gas under pressure into a sample container. One of the problems associated with the compressor method of forcing an environmental gas sample into a container is the fact that the sample could become contaminated due to the use of oils or other lubricants in the compressor.

SUMMARY OF THE INVENTION

An apparatus according to the present invention includes a sample bottle containing a metering orifice for admitting the gas to the interior of the bottle, contained within and cooled by a bath of liquid cryogen thus creating a partial vacuum inside the bottle to draw gas into the bottle where it is condensed and stored. Included as part of the apparatus is a cryogenic refrigerator disposed in an evacuated space above the liquid cryogen to condense liquid cryogen boil-off thus, maintaining the temperature of the sample bottle. As a further feature of the invention the cryogenic refrigeration space can be evacuated during start-up of the device to effect rapid cool-down to operating temperature.

Therefore, it is the primary object of the present invention to provide an improved apparatus for collecting and storing a sample of an environmental gas.

It is a further object of the present invention to provide an apparatus for collecting and storing a sample of environmental gas that can be rapidly cooled to working temperature.

It is still another object of the present invention to provide an apparatus for collecting and storing non-contaminated environmental gas samples.

It is yet another object of the present invention to provide an apparatus for collecting and storing noncontaminated environmental gas samples utilizing a closed cycle cryogenic refrigerator in combination with a liquid cryogen bath.

BRIEF DESCRIPTION OF THE DRAWING

FIG. 1 is a front elevational view, partially in section of an apparatus according the the present invention.

FIG. 2 is a top plan view of the apparatus of FIG. 1.

FIG. 3 is a left side elevational view of the crygenic refrigerator utilized in the present invention.

DETAILED DESCRIPTION OF THE PREFERRED EMBODIMENT

Referring to the drawing and in particular, FIG. 1, the numeral 10 indicates a sample bottle or container having a working pressure of 200 atmospheres max and a void volume at standard temperature and pressure of about 7 liters. Surrounding the neck 12 of sample bottle 10 is a support disc 14 which disc contains a plurality of appertures (not shown) for allowing fluid to pass through the disc 14 as well as for holding support rods 24 as will hereinafter be more fully explained. Bottle 10 is affixed to disc 14 by a pair of bottle supports 16, 18 each of which is fabricated from a thin metal strip (e.g. stainless steel) formed into a U shape containing a pair of bolts one of which is shown as 20 on the free end of strap 16 for fastening to disc 14 by a suitable nut 22 so that the disc 14 can be drawn tightly to the sample bottle 10. Projecting upwardly from disc 14 are a plurality of support legs (one of which is shown as 24) which are affixed to disc 14 as by bolts such as shown at 26. Legs 24 in turn fit into a warm flange 30 through use of a threaded portion 28 or like fastener as is well known in the art. Extending from the neck 12 of sample bottle 10 is conduit 32 of low thermal conductivity material such as stainless steel. Conduit 32 terminates in a manifold 34 mounted on flange 30 for fluid tight relation therewith by means of suitable sealing devices such as an O ring 36. Manifold includes a suitable valve 38 which communicates through the manifold 34 to conduit 32 to permit removal of the collected gas sample. Also mounted on manifold 34 is a metering orifice valve assembly 40 having a suitable inlet quick-connect fitting 42 to permit a hose or other device to be attached thereto. In addition, manifold 34 includes a pressure relief valve 44 set to open at a predetermined pressure to evacuate sample bottle 10 in the event of overpressurization. Manifold 34 includes a rupture disc 46 which is a fail-safe device set to rupture at a pressure higher than that which will cause safety relief valve 44 to open but at a pressure significantly lower than the rupture pressure of the sample bottle 10. Pipe plug 48 (FIG. 2) is included on manifold 34 to permit installation of additional accessories and to provide access to the manifold 34 for cleaning and the like.

Referring back to FIG. 1, the bottle 10 with bottle supports 16, 18 support disc 14, conduit 32 and supports 24 are constructed to fit within a vacuum jacketed Dewar 50 so that the Dewar 50 can contain the bottle 10 below the surface 53 of an inventory of liquid cryogen 51 (e.g. liquid nitrogen in the instance where air is being sampled). Dewar 50 has a closed end 52 and a open end 54 containing a flange 56. Flange 56 contains a plurality of radially disposed appertures 58 for receiving positioning pins (not shown) for positioning flange 30. Flange 56 includes an annular groove containing a suitable sealing device such as 0-ring 60. O-ring 60 permits vacuum tight sealing of plate 30 to flange 56 thus permitting evacuation of the interior portion of dewar 50 as will hereinafter be more fully explained.

As shown in FIGS. 1, 2 and 3, plate 30 has mounted thereon a cryogenic refrigerator 70. Refrigerator 70 is a single stage displacer-expander type refrigerator operated by a remote compressor (not shown) having a cold end 72 having thereon a cold shield 74. Model DE 102 available from Air Products and Chemicals, Inc., Allentown, Pennsylvania has been used for this device. Brazed or otherwise permanently affixed to cold shield 74 is a small electrical resistance heater 76 which, in turn, by means of electrical leads 78, extending through hermetically sealed feed through 80 (FIG. 3) is connected to a pressure control switch 82 mounted on top of refrigerator 70. Pressure control switch 82 is, in turn, through a suitable Tee 84 connected to a vacuum breaker valve 86 and conduit 88. Conduit 88 in turn, is connected through a manifold or Tee 90 to a conduit or passage 92, which passage 92 communicates to the interior of Dewar 50 when the refrigerator is installed to the plate 30 and plate 30 is placed on Dewar 50. Connected to the Tee element 90 is a control valve 94 the function of which will be hereinafter more fully explained.

Refrigerator 70 is held to flange 30 by a spring clamp assembly such as shown as 96 and 98 (FIG. 2).

Lastly, flange 30 includes handles 100, 102 so that the flange 30 together with the associated manifold 34, together with its sub assemblies conduit 32 and sample bottle 10 can be removed from the Dewar 50.

Refrigerator 70 includes the necessary electrical connection 104 to power the internal valve motor, and gas connections 106, 108 to admit to and remove from refrigerator 70 its normal working fluid.

In use, for sampling air, the device is assembled as shown with a supply of liquid nitrogen 51 introduced into the Dewar 50 through the refrigerator port 31 in flange 30 to cool sample bottle 10 to 77 degrees Kelvin (°K.). Alternatively, the liquid nitrogen can be charged into Dewar 50 and then bottle 10 can be slowly lowered into the bath contained in the Dewar so that the temperature of the sample bottle 10 and its attendant supports can be cooled from ambient temperature to 77° K.

After the liquid nitrogen 51 and bottle 10 are introduced into the Dewar, the refrigerator 70 is placed on the mounting flange 30 and is activated. In addition, to effect rapid cool-down from 77° K. to less than 73° K., a small vacuum pump is connected to valve 94 so that the space above the liquid nitrogen 52 in Dewar 50 can be rapidly evacuated. With the combination of refrigeration produced by refrigerator 70 and evacuation of the Dewar 50 it is possible to achieve a working temperature of less than 73° K. inside the Dewar, in less than 15 minutes time. A length of conduit containing in-line a suitable dryer or dryers (not shown), to remove moisture from the sample being collected as well as carbon dioxide to prevent freezing of the manifold 34, is fitted to quick connect fitting 42. The conduit ahead of the dryers is disposed in the area in which the sample is to be taken. As explained in the specification of U.S. Patent Application Ser. No. 956,312, cooling of the sample bottle 10 creates a partial vacuum within bottle 10, thus permitting air to be drawn through metering orifice valve 40 into the sample bottle 10. Because of the liquid nitrogen the air sample is condensed inside bottle 10.

As is well known in the art, liquid nitrogen will begin to boil off due to heat infiltration through the Dewar 50. Refrigerator 70 continuously provides a temperature of less than 73° K. to condense nitrogen boil off. In view of the fact that the refrigerator is operating below 77° K., nitrogen will condense on the cold end 72 of refrigerator 70. Heater 76 is included to prevent nitrogen from freezing on the cold end 72 of refrigerator 70 and is activated by pressure switch 82 sensing a decrease in pressure inside the vacuum space above the liquid nitrogen.

Plate 30 need not be bolted to flange 56 since the vacuum inside the Dewar 50 will cause a sealing of the plate 30 to the flange 34. This vacuum sealing also acts as a safety relief valve since if the pressure increases inside the Dewar 50 the plate 30 can be displaced by increased pressure of the warmed gaseous nitrogen inside Dewar 50.

An apparatus according to the invention was constructed utilizing a Dewar 50 having an 18 centimeter inside diameter with a 91 centimeter deep inner container. Dewar 50 was filled with nitrogen to a level that would allow for the loss of approximately 3 liters during cool-down. For a normal 7 liter sample bottle 10, a sample flow rate of from 25 millimeters per minute to 200 milliliters per minute can be utilized. A total volume of 1,400 standard liters at 21° C. was collected. Collecting 1,400 standard liters did not activate pressure relief valve 44 or burst disc 46 when the sample bottle 10 and its attendant assembly was removed from the dewar 50. In the event bottle 10 is maintained within the Dewar containing liquid nitrogen until it is returned to the laboratory for sampling a 2,000 standard liter sample can be collected.

In the unit that was built and tested the pressure switch 82 was set so that the heater 76 on cold end 72 of refrigerator 70 was turned on when the dewar pressure dropped below 24 centimeters of mercury. When the pressure inside the Dewar rose to a level of 30 centimeters of mercury the heater 76 is turned off thus maintaining a temperature within the space above the liquid cryogen between 70° and 73° K. The pressure temperature relation for liquid nitrogen is well known.

For a device according to the present invention utilizing a bottle having a 200 atmosphere working pressure the reseatable pressure relief valve 44 is set to open at 200 atmospheres and the burst disc 46 to rupture at 220 atmoshpheres, both of which are well below the burst strength of a 200 atmosphere bottle such as 10 and the associated conduit 32 and manifold 34.

Having thus described my invention, what is claimed and desired to be secured by Letters Patent of the United States is set forth in the appended claims:

1. An apparatus for collecting and storing a sample of environmental gas comprising in combination:
   means to removably confine a sample bottle, said bottle having a metering orifice through which environmental gas can enter, in a bath of liquid cryogen said means including an evacuable space above said sample bottle allowing for liquid cryogen to boil-off and be confined therein;
   means to condense said cryogen boil-off thus maintaining said sample bottle at a temperature of just below the normal boiling temperature of said liquid cryogen; and
   means to effect rapid cool-down of said sample bottle.

2. An apparatus according to claim 1 wherein said means to removably confine said sample bottle includes a support plate to sealingly engage a complimentary surface on a vacuum dewar.

3. An apparatus according to claim 1 wherein said means to condense said cryogen boil-off includes a cryogenic refrigerator removably disposed within said evacuable space above said liquid cryogen.

4. An apparatus according to claim 1 wherein said refrigerator includes a heater disposed around its cold end said heater operated by a pressure controller connected to said evacuable space to prevent cryogen freeze out on said cold end of said refrigerator.

5. An apparatus according to claim 1 wherein said means to effect rapid cool-down of said sample bottle includes means to evacuate said evacuable space.

* * * * *